United States Patent [19]

Riebel

[11] Patent Number: 4,801,709

[45] Date of Patent: Jan. 31, 1989

[54] PROCESS FOR THE PREPARATION OF 2-CYANAMINO-4,6-DIALKOXY-1,3,5-TRIAZINES

[75] Inventor: Hans-Jochem Riebel, Wuppertal, Fed. Rep. of Germany

[73] Assignee: Bayer Aktiengesellschaft, Leverkusen, Fed. Rep. of Germany

[21] Appl. No.: 125,621

[22] Filed: Nov. 25, 1987

Related U.S. Application Data

[63] Continuation-in-part of Ser. No. 851,059, Apr. 11, 1986.

[30] Foreign Application Priority Data

Apr. 27, 1985 [DE] Fed. Rep. of Germany ....... 3515286

[51] Int. Cl.[4] .......................................... C07D 251/46
[52] U.S. Cl. .................................................... 544/194
[58] Field of Search ........................................ 544/194

[56] References Cited

U.S. PATENT DOCUMENTS 3,317,528  5/1967  Tsuda et al. ......................... 544/194
3,758,470  9/1973  Ackermann et al. .

FOREIGN PATENT DOCUMENTS 2050948  11/1971  Fed. Rep. of Germany .
2263853  12/1972  Fed. Rep. of Germany ...... 544/194
1052567  12/1966  United Kingdom .

OTHER PUBLICATIONS

Chemical Abstracts, vol. 94, pp. 1 and 656 (May 11, 1981).
Organikum, Organisch–Chemisches Grundpraktikum Von Einem Autorenkollektiv der Technischen Universitat Dresden (3, uberarbeitete Auflage), Veb Deutscher Verlag Der Wissenschaften, Berlin 1964, p. 389.
Title Page DOS 2,050,948.

*Primary Examiner*—John M. Ford
*Attorney, Agent, or Firm*—Sprung Horn Kramer & Woods

[57] ABSTRACT

A process for the preparation of a 2-cyanamino-4,6-dialkoxy-1,3,5-triazine of the formula

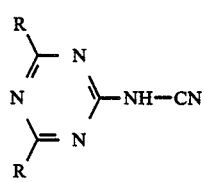

in which
R represents alkoxy, comprising reacting 2,4,6-trichloro-1,3,5-triazine with cyanamide under alkaline conditions thereby to produce a 2-cyanamino-4,6-dichloro-1,3,5-triazine of the formula

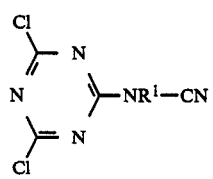

in which
R[1] represents an alkali metal ion, reacting the 2-cyanamino-4,6-dichloro-1,3,5-triazine with at least twice the molar amount of an alcoholate of the formula RMe in which
Me is an alkali metal ion, in the presence of a diluent, and then reacting with acid in the presence of water. The end product is a known intermediate for synthesizing herbicides.

1 Claim, No Drawings

PROCESS FOR THE PREPARATION OF 2-CYANAMINO-4,6-DIALKOXY-1,3,5-TRIAZINES

This is a continuation-in-part of application Ser. No. 851,059, filed Apr. 11, 1986, now pending.

The present invention relates to a new process for the preparation of 2-cyanamino-4,6-dialkoxy-1,3,5-triazines which can be used as intermediates for the preparation of herbicides and plant-growth regulators.

It has already been disclosed that 2-cyanamino-1,3,5-triazines are obtained by reaction of alkali metal or alkaline earth metal salts of cyanamide with the appropriate 2-halogeno-1,3,5-triazines (compare, for example, DE-OS (German Published Specification) 3,334,455/European Patent A-121,082). However, this process is of only very limited applicability because of unsatisfactory preparation methods for the required starting materials. Thus, there is a need for a new, widely applicable, preparation process for 2-cyanamino-4,6-dialkoxy-1,3,5-triazines.

It has now been found that 2-cyanamino-4,6-dialkoxy-1,3,5-triazines of the general formula (I)

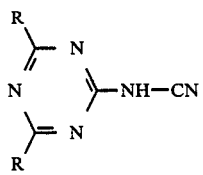
(I)

in which
R represents alkoxy, are obtained when 2-cyanamino-4,6-dichloro-1,3,5-triazines of the formula (II)

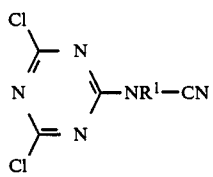
(II)

in which
$R^1$ represents one equivalent of an alkali metal ion, are reacted with at least twice the molar amount of alcoholate of the formula (III)

RMe (III)

in which
R has the abovementioned meaning, and
Me represents one equivalent of an alkali metal ion, in the presence of diluents, then water is added and the mixture is acidified.

Surprisingly, it is possible with this process according to the invention to obtain the compounds of the formula (I) in good yields. In the preparation of the compounds of the formula (I) according to the state of the art from alkali metal or alkaline earth metal salts of cyanamide and the appropriate halogeno-1,3,5-triazines the yields are very unsatisfactory.

Those compounds of the formula (I) which are preferably prepared by use of the process according to the invention are those in which
R represents alkoxy having 1 to 6 carbon atoms.

Those compounds of the formula (I) which are particularly preferably prepared are those in which
R represents methoxy, ethoxy, n-propoxy, i-propoxy, n-butoxy, i-butoxy, sec.-butoxy or tert.-butoxy.

Those compounds of the formula (I) which are very particularly preferably prepared are those in which
R represents methoxy, ethoxy, n-propoxy, i-propoxy or n-butoxy.

When, for example, the sodium salt of 2-cyanamino-4,6-dichloro-1,3,5-triazine and sodium ethylate are used as starting materials for the process according to the invention, then the reaction can be represented by the equation below:

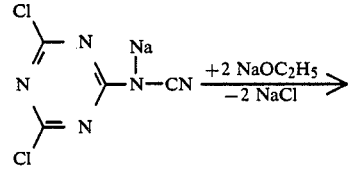

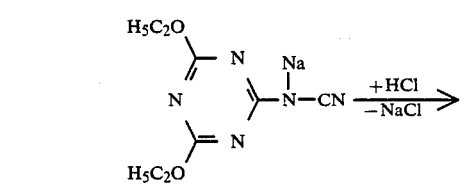

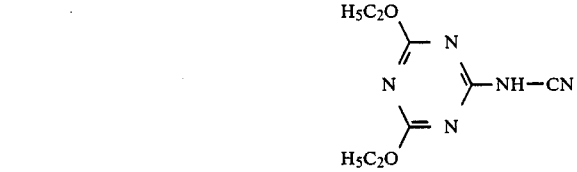

The 2-cyanamino-4,6-dichloro-1,3,5-triazines which are to be used as starting materials for the process according to the invention are generally defined by the formula (II). In this formula, R preferably represents those radicals which have been indicated above as being preferred or particularly preferred within the scope of the definition of substituents in the formula (I). $R^1$ in this formula represents one equivalent of an alkali metal ion, such as, in particular, one sodium or potassium ion. $R^1$ preferably represents a sodium ion.

The following may be mentioned as examples of compounds of the formula (II):
the sodium or potassium salt of 2-cyanamino-4,6-dichloro-1,3,5-triazine.

The compounds of the formula (II) are known (compare, for example, DE-AS (German Published Specification) 2,050,948).

The alcoholates which are also to be used as starting materials for the process according to the invention are generally defined by the formula (III). In this formula, R preferably or in particular has the same meanings as mentioned above as preferred or particularly preferred within the scope of the definition of substituents in the formula (I). In this formula, Me preferably represents a sodium or potassium ion.

The following may be mentioned as examples of compounds of the formula (III):
sodium methylate, ethylate, n-propylate, i-propylate, n-butylate, i-butylate, sec.-butylate and tert.-butylate, and the corresponding potassium derivatives.

The compounds of the formula (III) are generally known compounds of organic chemistry.

The process according to the invention is carried out in the presence of diluents. These include, in particular, aliphatic and aromatic hydrocarbons such as pentane, hexane, heptane, cyclohexane, petroleum ether, benzine, ligroin, benzene, toluene and xylene; alcohols such as methanol, ethanol, n-propanol, i-propanol, n-butanol, i-butanol, sec.-butanol and tert.-butanol; ketones such as acetone, methyl ethyl, methyl isopropyl and methyl isobutyl ketones; nitriles such as, for example, acetonitrile and propionitrile; amides such as, for example, dimethylformamide, dimethylacetamide and N-methylpyrrolidone, and dimethyl sulphoxide, tetramethylene sulphone and hexamethylphosphoric triamide. The alcohols corresponding to the alcoholates of the formula (III) which are used are preferably employed.

The process according to the invention is generally carried out at temperatures between 0° C. and 60° C., preferably between 0° C. and 40° C. The reactions are generally carried out under atmospheric pressure.

In carrying out the process according to the invention, 2.0 to 2.5 mols, preferably 2.0 to 2.3 mols, of alcoholate of the formula (III) are used for each mol of the compound of the formula (II). The working up of the compound of the formula (I) is carried out by usual methods. After addition of the starting materials is complete, stirring is continued for a short time or for several hours at 15° C. to 25° C. The mixture is then evaporated, and water is added to the residue and acidified with a mineral acid such as, for example, hydrochloric acid. The compounds of the formula (I) generally result in the form of crystals.

The 2-cyanamino-4,6-dialkoxy-1,3,5-triazines to be prepared by the process according to the invention can be used as intermediates for the preparation of guanidine derivatives which are active as herbicides and plant-growth regulators (compare EP-OS (European Published Specificiation) 121,082).

PREPARATION EXAMPLES

Example 1

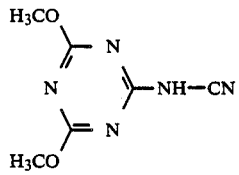

A solution of 6.9 g (0.3 mol) of sodium in 50 ml of methanol is added dropwise to a suspension of 30 g (0.14 mol) of 2-cyanamino-4,6-dichloro-1,3,5-triazine sodium salt in 200 ml of methanol in such a manner that a temperature of 40° C. is not exceeded. The mixture is then stirred at 20° C. for 2 hours, filtered and the filtrate is evaporated. The residue is dissolved in 50 ml of water and acidified with hydrochloric acid. The resulting crystals are filtered off with suction and dried.

22.6 (89% of theory) of 2-cyanamino-4,6-dimethoxy-1,3,5-triazine are obtained. The product is characterized by $^1$H-NMR spectra.

Example 2

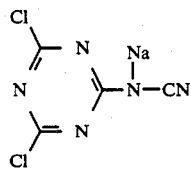

(a) according to DE-AS 2,050,948 (pp. 16/17)

A solution of 17.5 g (0.2 mol) of the di-sodium salt of cyanamide ($Na_2N-CN$) in 100 ml of water is added dropwise at 0°–10° C. to a stirred mixture of 37 g (0.2 mol) of 2,4,6-trichloro-1,3,5-triazine (=cyanuric chloride), 20 ml of acetone and 200 ml of ice-water, maintaining the pH of the reaction mixture of 9.0–10.0. The mixture is then stirred at 0°–5° C. for 15 hours, and the resulting crystals are filtered off with suction and dried.

32 g (75% of theory) of the sodium salt of 2-cyanamino-4,6-dichloro-1,3,5-triazine are obtained; melting point: >250° C.

(b) according to this invention

A solution of 88 g (2.1 mol) of cyanamide ($H_2N-CN$) and 176 g (4.4 mol) of sodium hydroxide in 500 ml of water is added dropwise, within 2 hours, at 0°–10° C. to a stirred mixture of 370 g (2.0 mol) of 2,4,6-trichloro-1,3,5-triazine (=cyanuric chloride) and 1500 ml of ice-water. The reaction mixture is then stirred at about 10° C. for further 2 hours, and the resulting crystals are filtered off with suction and dried.

403 g (95% of theory) of the sodium salt of 2-cyanamino-4,6-dichloro-1,3,5-triazine are obtained; melting point: >250° C.

It will be understood that the specification and examples are illustrative but not limitative of the present invention and that other embodiments within the spirit and scope of the invention will suggest themselves to those skilled in the art.

What is claimed is:

1. A process for the preparation of a 2-cyanamino-4,6-dialkoxy-1,3,5-triazine of the formula

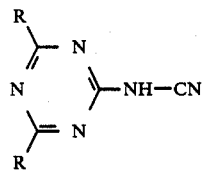

in which
R represents alkoxy, comprising reacting 2,4,6-trichloro-1,3,5-triazine with cyanamide under alkaline conditions thereby to produce a 2-cyanamino-4,6-dichloro-1,3,5-triazine of the formula

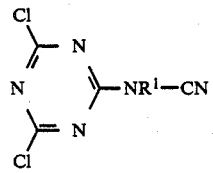

in which
$R^1$ represents an alkali metal ion, reacting the 2-cyanamino-4,6-dichloro-1,3,5-triazine with at least twice the molar amount of an alcoholate of the formula RMe in which
Me is an alkali metal ion, in the presence of a diluent, and then reacting with acid in the presence of water.

* * * * *